(12) United States Patent
Wilkinson et al.

(10) Patent No.: US 6,508,987 B1
(45) Date of Patent: Jan. 21, 2003

(54) BIOLOGICAL FLUID COLLECTION DEVICE WITH A PIVOTABLE FAUCET

(75) Inventors: Bradley M. Wilkinson, North Haledon, NJ (US); Robert S. Golabek, Jr., Towaco, NJ (US)

(73) Assignee: Becton, Dickinson and Company, Franklin Lakes, NJ (US)

(*) Notice: Subject to any disclaimer, the term of this patent is extended or adjusted under 35 U.S.C. 154(b) by 0 days.

(21) Appl. No.: 09/369,997

(22) Filed: Aug. 6, 1999

(51) Int. Cl.[7] .................................................. B01L 3/00
(52) U.S. Cl. ........................ 422/102; 422/103; 222/556
(58) Field of Search ................................. 422/100, 102, 422/103; 222/556; 215/235; 210/533, 534, 535, 536; 600/573

(56) References Cited

U.S. PATENT DOCUMENTS

| | | |
|---|---|---|
| 3,750,647 A | 8/1973 | Gleason et al. |
| 4,106,490 A | 8/1978 | Spilman et al. |
| 4,116,066 A | 9/1978 | Mehl et al. |
| 4,121,306 A | 10/1978 | Bringman et al. |
| 4,258,032 A | 3/1981 | Mehl |
| 4,300,404 A | 11/1981 | Mehl et al. ............... 73/863.52 |
| 4,335,730 A | 6/1982 | Griffin |
| 4,393,881 A | 7/1983 | Shah |
| 4,492,258 A | 1/1985 | Lichtenstein et al. |
| 4,761,379 A | 8/1988 | Williams et al. |
| 4,769,215 A | 9/1988 | Ehrenkranz ................... 422/58 |
| 4,895,167 A | 1/1990 | Guala |
| 4,930,666 A * | 6/1990 | Rudick |
| 4,934,420 A * | 6/1990 | Radna |
| 5,069,878 A | 12/1991 | Ehrenkranz ................... 422/61 |
| 5,147,342 A | 9/1992 | Kane et al. .................. 604/356 |
| 5,251,639 A | 10/1993 | Rentsch |
| 5,422,076 A | 6/1995 | Jones ......................... 422/102 |
| 5,569,225 A | 10/1996 | Fleury ........................ 604/323 |
| 5,797,855 A | 8/1998 | Hazard et al. |
| 5,849,505 A | 12/1998 | Guirguis |
| 5,893,176 A | 4/1999 | Magiera et al. |
| 5,894,607 A | 4/1999 | Van Den Burg |
| 5,894,608 A | 4/1999 | Birbara |
| 5,897,840 A | 4/1999 | Owens, Jr. et al. ......... 422/102 |
| 5,913,435 A * | 6/1999 | Fuchs |
| 6,170,719 B1 * | 1/2001 | Wilkinson et al. |
| 6,171,261 B1 * | 1/2001 | Niermann et al. |
| 6,235,010 B1 * | 5/2001 | Wilkinson et al. |

* cited by examiner

*Primary Examiner*—John Kim
*Assistant Examiner*—David Sorkin
(74) *Attorney, Agent, or Firm*—Nanette S. Thomas, Esq.

(57) ABSTRACT

A biological fluid collection device with a pivotable faucet is disclosed. The device is designed to collect, hold and transfer a biological specimen into a non-evacuated tube through an integrated pivotable faucet component. This device uses no needles, either blunt or sharp, and provides safety from needle puncture. The device works with a non-evacuated tube and a specially designed cap that attaches to the container via the pivotable faucet. The device includes a container for collecting, holding and transferring the biological fluid. The design of the container facilitates use of the tube as a handle in order to position the container to receive collection of the biological fluids. The method of collection begins with using the non-evacuated tube as a handle to hold the container and collecting the biological specimen in the container. A lid is attached to the top of the container to prevent contamination and exposure to the specimen during transfer into the non-evacuated tube. The non-evacuated tube is rotated and stopped in place by a detent. The transfer of the biological fluid is without any contact to the liquid specimen. Gravity allows the liquid to transfer. Liquid transfer is stopped by rotation of the tube and pivotable faucet. The tube is rotated back to its original position as a handle and pulled off the container. The second tube may be filled at that time or the container can be discarded for proper disposal.

17 Claims, 8 Drawing Sheets

BIOLOGICAL FLUID COLLECTION DEVICE WITH A PIVOTABLE FAUCET

BACKGROUND OF THE INVENTION

1. Field of Invention

The invention relates generally to an apparatus for collecting and transferring biological fluids. More particularly, the present invention relates to a biological fluid collection device with a pivotable faucet for collecting and transferring a fluid specimen to a collection tube.

2. Description of Prior Art

Biological fluids are collected periodically for laboratory analysis. Laboratory equipment that performs the analysis may only accept biological fluids stored in a test tube. However, a test tube is too small for the convenient collection of many biological fluids, such as urine. As a result, specimens often are collected in a fairly large container. After collection of the fluid in the container, the container is delivered to a medical technician. The technician then transfers a portion of the fluid to a collection tube that can be sealed and transported to a laboratory for analysis. The transfer of biological fluid from the collection container to the collection tube is an unpleasant task that creates the risk of contaminating the specimen or exposing the medical technician to potentially harmful pathogens in the specimen.

In urine specimen collection, vacuum tubes are usually not very useful because vacuum tubes usually have a limited shelf life due to a gradual migration of gas molecules through the walls of the tube. Some prior art collection containers have a test tube that is attached. In this prior art device, a portion of the specimen in the container is automatically transferred to the tube. The tube then may be separated from the container, sealed and shipped to a laboratory for analysis. However, these prior art assemblies can lead to leakage during the initial collection of the specimen or after the separation of the test tube from the collection container. Additionally, control of the volume of the specimen in the test tube may vary from sample to sample. A means for controlling the volume in each specimen sample taken is needed to assure accurate results in the subsequent laboratory analysis. Also, the use of a non-sharp or blunt cannula in the transfer of the specimen from the collection container to the tube is preferred to avoid potential skin puncturing of the medical technician. A collection container designed to avoid human contact during transfer of the specimen is desired in order to prevent specimen contamination. Also, there is a need for a collection container to use a non-evacuated vacuum tube to avoid the potential limited shelf life of the vacuum tube.

SUMMARY OF THE INVENTION

The present invention alleviates in great part the drawbacks associated with the prior art biological fluid collection devices. Provided is a biological fluid collection device comprising a container for holding the fluid having an upper open portion, a lower portion and side walls therebetween. The container further includes an orifice through the container at a low gravitational point inside the container. A projecting faucet pivotably attached to the container is also provided. The faucet is in fluid communication with the orifice. The orifice and faucet can be disposed on either the lower portion or side walls. The pivotable faucet has closed and open positions. Because the faucet has open and closed positions, pivoting or rotation of the faucet controls the fluid transfer from the container.

Further included in the device is a tube having a closed bottom, an open top and side walls therebetween. The tube used in the biological fluid collection device is preferably non-evacuated. However, an evacuated tube may be used in this device. The tube further includes a cap disposed on the open top. The cap has an off-centered hole therethrough for receiving the pivotable faucet in releasable locking engagement. Thus, no needles, either blunt or sharp, are used in the transfer of the fluid from the container to the tube. The cap on the test tube further includes a closure lid hingedly attached to the cap for permanently sealing the cap after fluid collection. A plug on the closure lid mates with the hole in the cap to provide a leak-resistant seal.

The faucet rotates in a closed position when the tube is used as a handle for holding the container during collection. The faucet is rotated in the open position when the fluid flows through the hole into the tube. When the orifice and pivotable faucet are disposed on the lower portion, the biological fluid collection device can further comprise an annular skirt attached to the lower portion. The annular skirt has a planar bottom for flat surface support. The annular skirt further includes a recessed portion for securing the tube in the closed position. Also included in the biological fluid device, when the orifice and faucet are disposed on the lower portion, is a detent mounted on the annular skirt. The purpose for the detent is for securing the tube in the open position. The detent also has a planar bottom for assisting in flat surface support.

When the orifice and pivotable faucet are disposed on the side walls of the container, the side walls have a recessed portion for securing the tube in the closed position. In this embodiment, the lower portion is substantially planar for providing flat surface support.

The biological fluid collection device further comprises a lid disposed on the upper portion of the container for protecting the fluid in the container from contamination. The lid on the biological fluid collection device further comprises a vent which allows air flow during the transfer process to the tube. The vent contains a membrane which is disposed on the lid. The membrane allows the air flow through the vent and prevents fluid flow through the lid.

The biological fluid collection device can further include depressions on the side walls for assisting and gripping the container. The container could also include snap fits mounted to the lower portion to hold the tube during storage.

BRIEF DESCRIPTION OF THE DRAWINGS

The invention is now described in greater detail by way of reference to the following drawings wherein.

DETAILED DESCRIPTION OF THE INVENTION

Turning now to the drawings, wherein like numerals denote like components, FIGS. 1–11 depict a biological fluid collection device with a pivotable faucet generally shown as numeral 8. Device 8 comprises a container 10, a tube 40, and a projecting faucet 30. Container 10 is for collecting, holding, and transferring the fluid. Container 10 has an upper portion 12, a lower portion 14, and side walls 20 therebetween. Preferably, side walls 20 are cylindrically shaped. However, such a shape is not necessary for device 8 to function. Other such shapes for side walls 20 include oblong shaped, elliptical shaped, contoured shaped, and rectangularly shaped side walls. Container 10 further includes an orifice 22 through container 10. Orifice 22 is located at a low gravitational point 24 inside container 10. Low gravitational point 24 need not be the lowest gravitational point in container 10 for device 8 to function. All that is needed for device 8 to transfer the fluid within is that orifice 22 is at a low gravity point.

Figure 6:
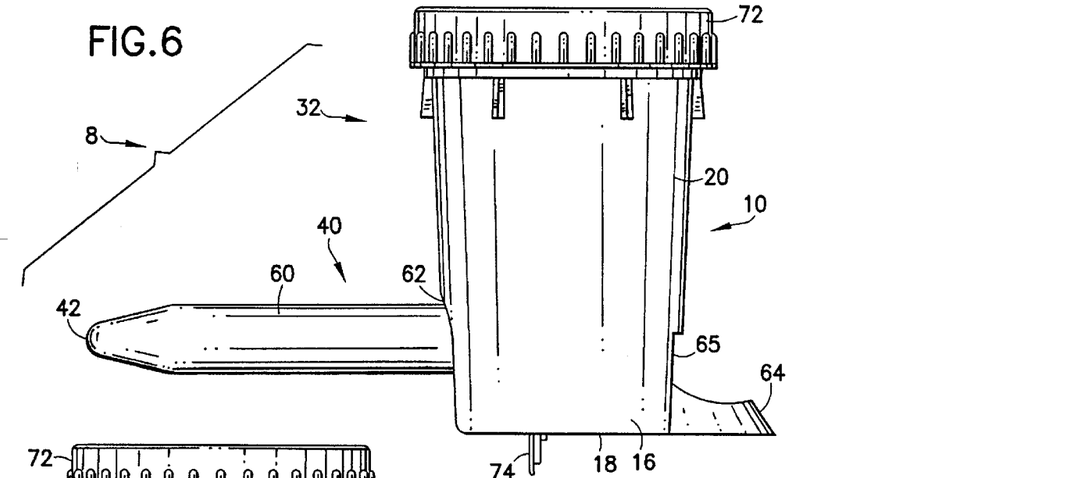
FIG. 6 is a side view of the biological fluid collection device assembled with a tube positioned in the closed position.
Figure 7:
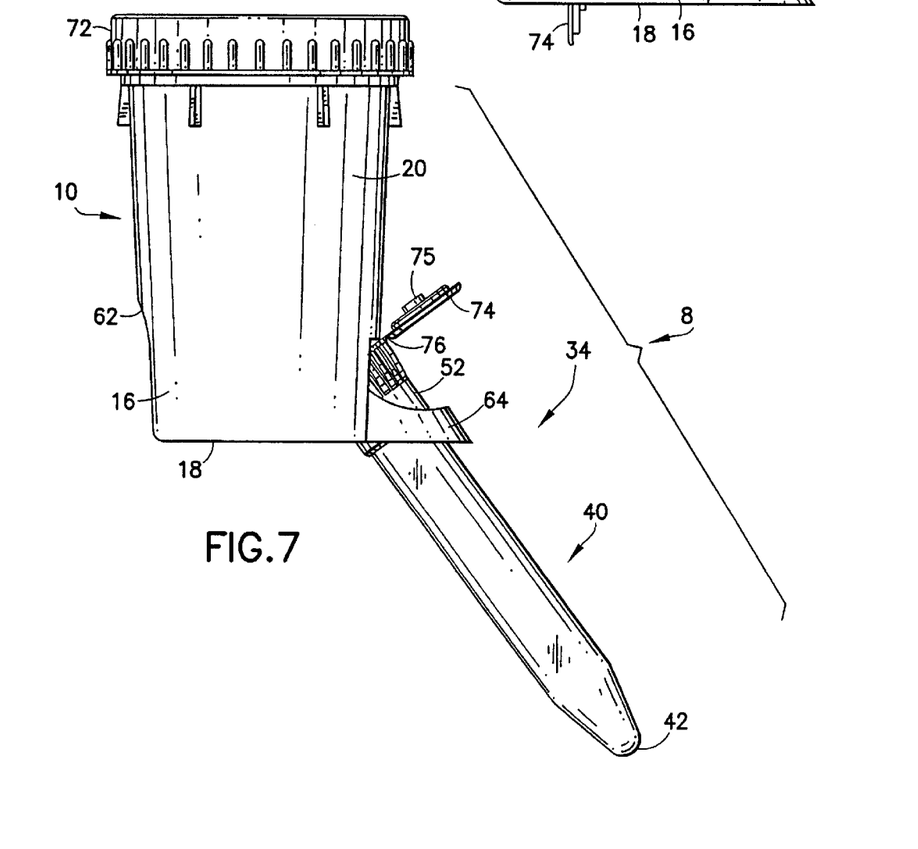
FIG. 7 is a side view of the biological fluid collection device assembled with a tube in the open position.
Figure 10:
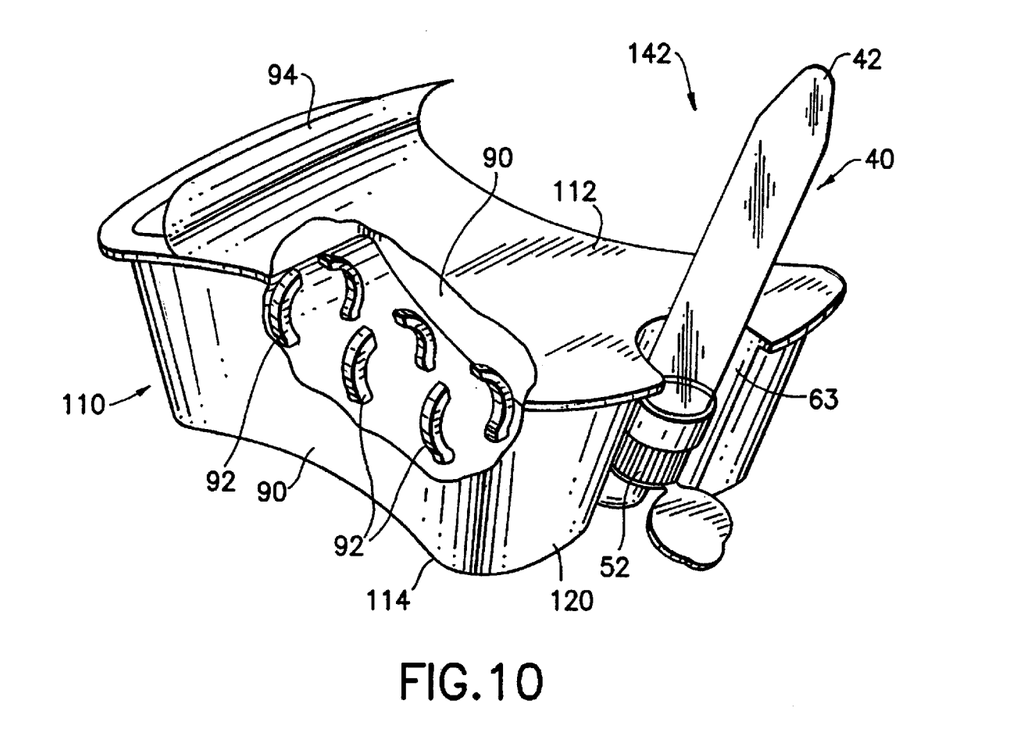
FIG. 10 is a perspective view of an alternate embodiment of the biological fluid collection device in FIG. 6 in the closed position.
Figure 11:
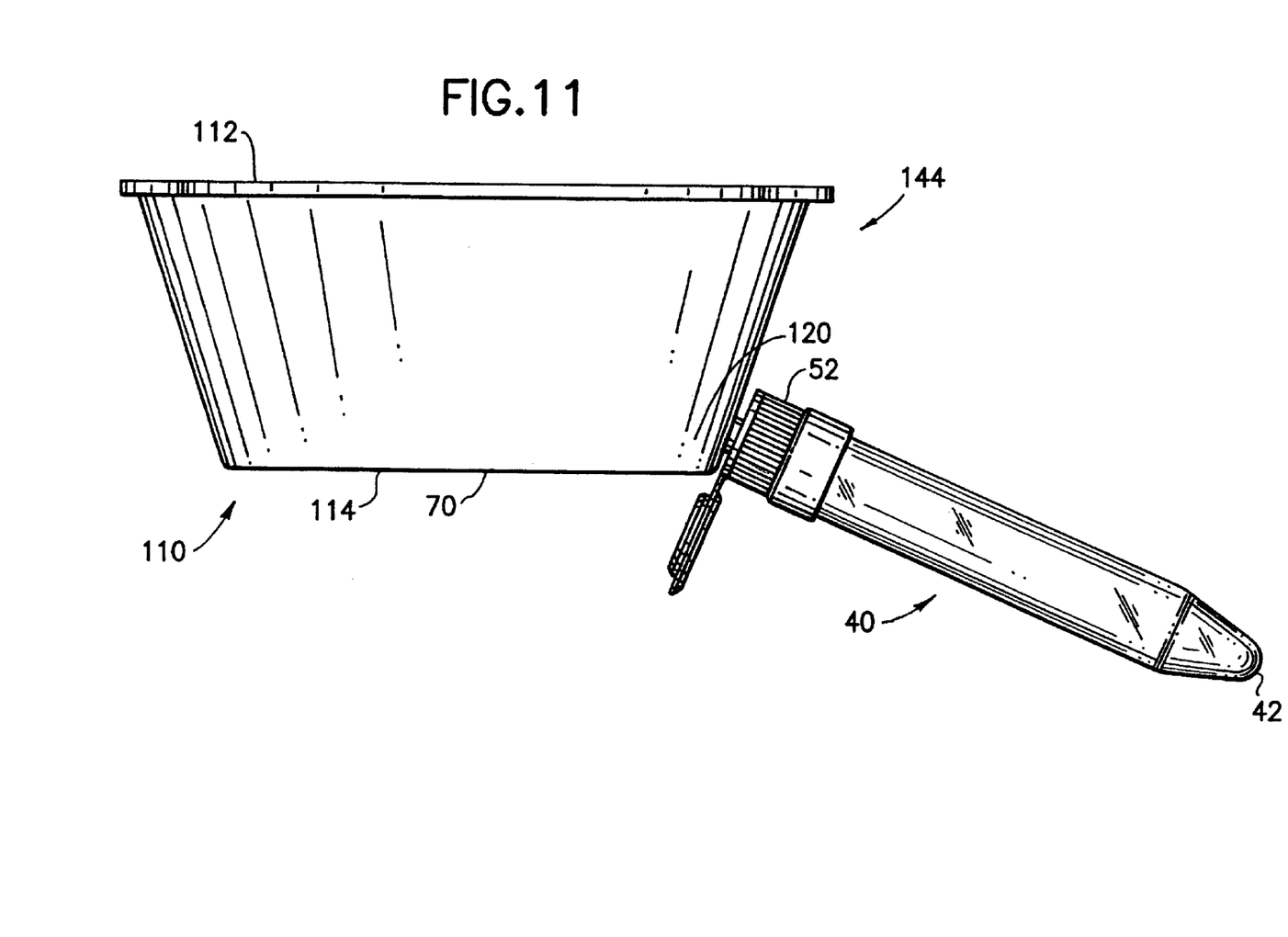
FIG. 11 is a side view of the device in FIG. 10 in the open position.

Projecting faucet 30 is pivotably attached to container 10 and in fluid communication with orifice 22. Pivotable faucet 30 has a closed position 32 and an open position 34 as shown in FIGS. 6 and 7, respectively. Orifice 22 and pivotable faucet 30 are preferably disposed on lower portion 14. However, orifice 22 and pivotable faucet 30 may be disposed on side walls 20 as shown in FIGS. 10 and 11.

Figure 5:
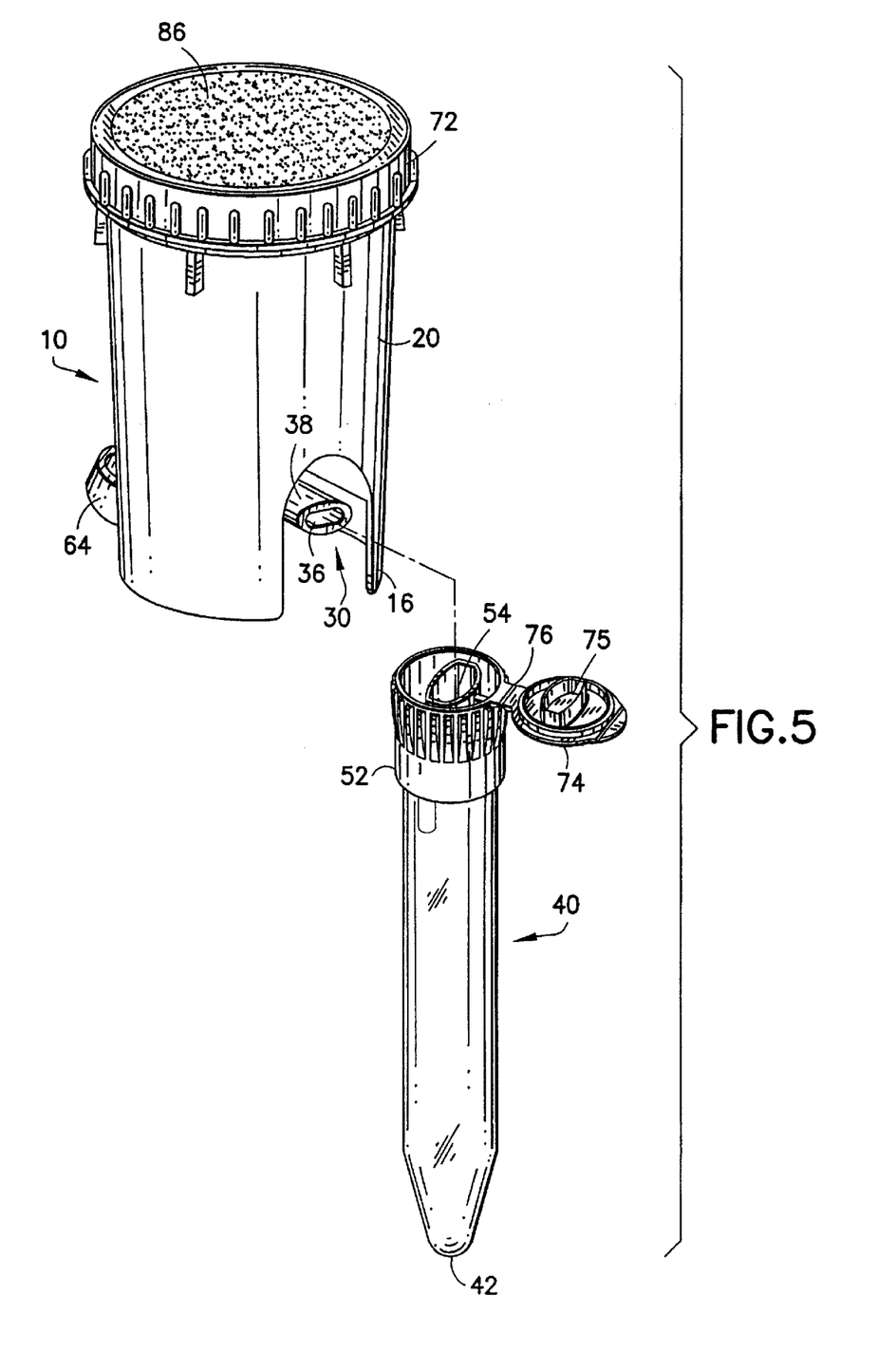
FIG. 5 is an exploded front perspective view of the biological fluid collection device in FIG. 2 in conjunction with a tube.
Figure 8:
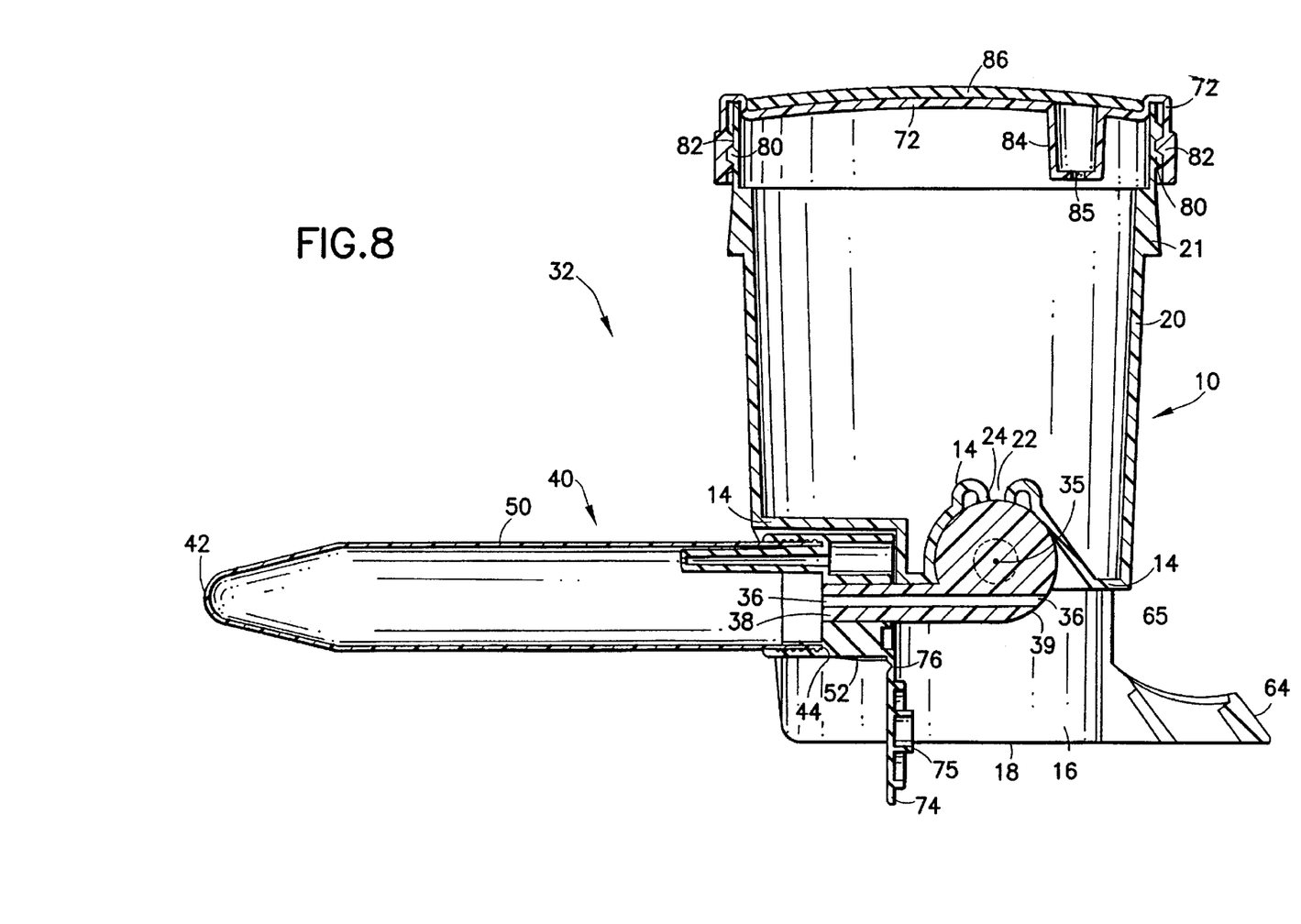
FIG. 8 is a cross-sectional view of FIG. 6.
Figure 9:
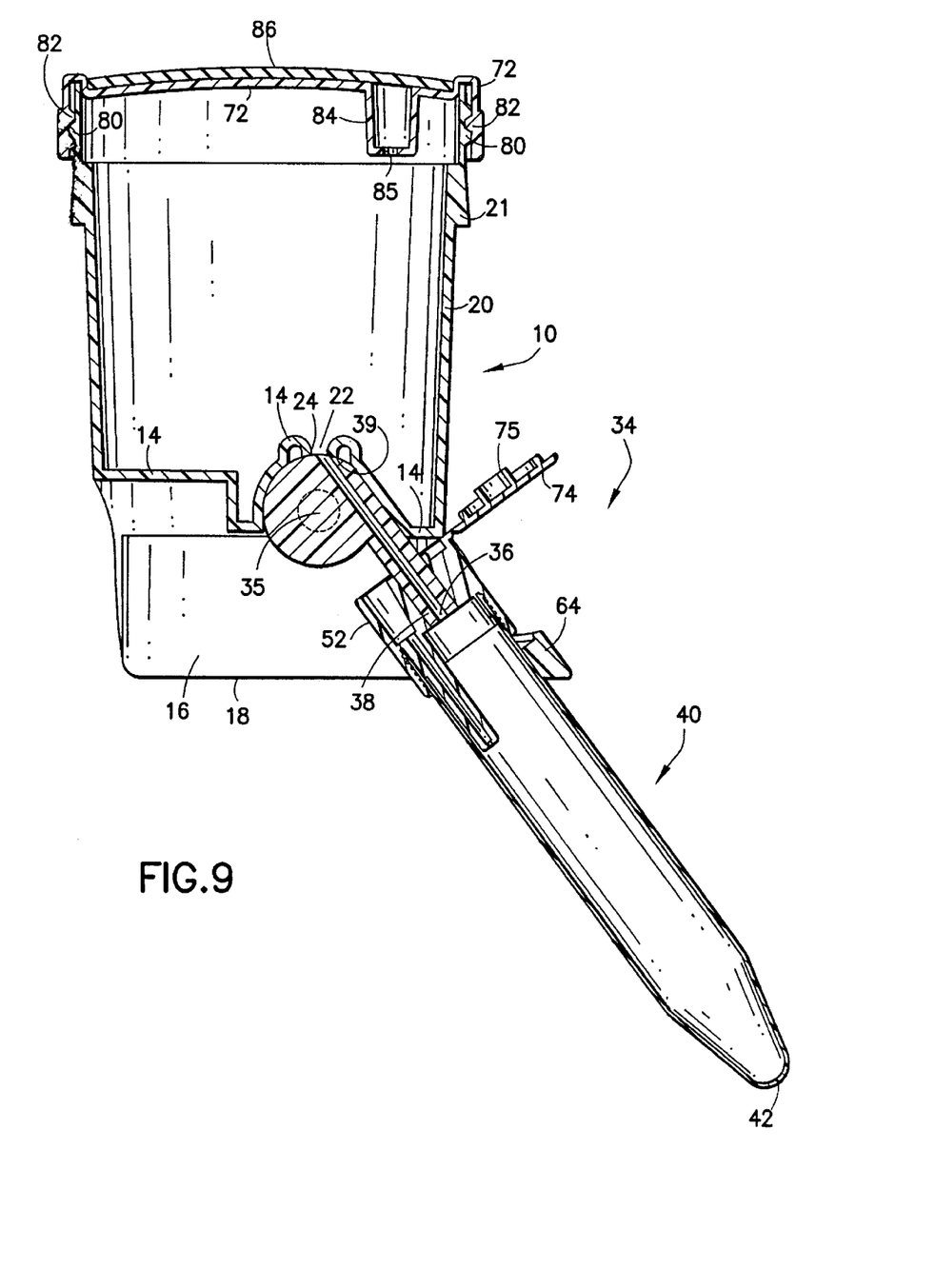
FIG. 9 is a cross-sectional view of FIG. 7.

Pivotable faucet 30 is further characterized as shown in FIG. 5 to include a conduit 36 therethrough, a male distal end 38 and a proximal end 39. Male distal end 38 attaches to a cap 52 on tube 40. Cap 52 has a hole 54 which male distal end 38 enters into for secure and releasable attachment. Hole 54 is off-centered to provide maximum clearance for attachment of tube 40 to container 10 and for tube 40 to pivot. Thus, no needle cannula, either sharp or blunt, is required for the transfer of fluid from container 10 to tube 40. Preferably, tube 40 is attached to container 10 prior to collection. However, tube 40 does not have to be connected to container 10 for device 8 to function. If tube 40 is not attached to container 10 during collection, faucet 30 must be in closed position 32, otherwise fluid comes out of male distal end 38. Thus, after tube 40 is removed from container 10 when transfer is completed, fluid will leak out unless faucet is placed in closed position 32. This attachment is seen in FIG. 8 and FIG. 9. Faucet 30 also has a pivot point 35. When faucet 30 is pivoted about point 35 and conduit 36 at proximal end 39 is in fluid communication with orifice 22, faucet 30 is opened and fluid transfer from container 10 commences. Conversely, when faucet 30 is pivoted so that conduit 36 at proximal end 39 is not in fluid communication with orifice 22, faucet 30 is closed and no fluid transfer commences. Thus, pivotable faucet 30 controls the amount of fluid that is transferred out of container 10.

Tube 40 as shown in FIGS. 5–9 is further included in device 8. Tube 40 is characterized by a closed bottom 42, an open top 44 and cylindrical side walls 50 therebetween. Preferably, tube 40 is a non-evacuated tube for collection purposes. However, an evacuated tube may be used. A non-evacuated tube is preferred because there is no shelf-life for the vacuum which pulls the fluid in the tube. In the present invention, gravity pulls the fluid from container 10 into tube 40. Tube 40 further includes cap 52 disposed on open top 44. There are many methods for cap 52 to be disposed on open top 44. Such methods include thread attachment, snap-fittings, and mechanical fasteners.

Hole 54 is through cap 52 for receiving male distal end 38 of faucet 30 in releasably locking engagement. Hole 54 is off-centered with respect to the center point of cap 52. The function of this geometry is to provide maximum clearance for tube 40 to pivot when tube 40 is connected to faucet 30. Faucet 30 is in closed position 32 when tube 40 is perpendicular to container 10. Tube 40 is then used as a handle 60 for holding container 10 during collection. Faucet 30 is rotated in open position 34 when fluid flows through hole 54 into tube 40. Rotation of faucet 30 is enabled by pivoting tube 40.

Lower portion 14 is characterized by an annular skirt 16. Annular skirt 16 is attached to the bottom of lower portion 14. Preferably, in this embodiment, annular skirt 16 and lower portion 14 are a unitary structure and made of the same material. However, both may be separate components mounted together. Methods for mounting include ultra-sonic welding, adhesive bonding, and mechanical fasteners. Annular skirt 16 is further characterized by having a planar bottom 18 for flat surface support. Thus, device 8 can be placed on a flat surface without tipping over. Annular skirt 16 is also characterized by having a recessed portion 62 for securing tube 40 in closed position 32.

Figures 1, 2:
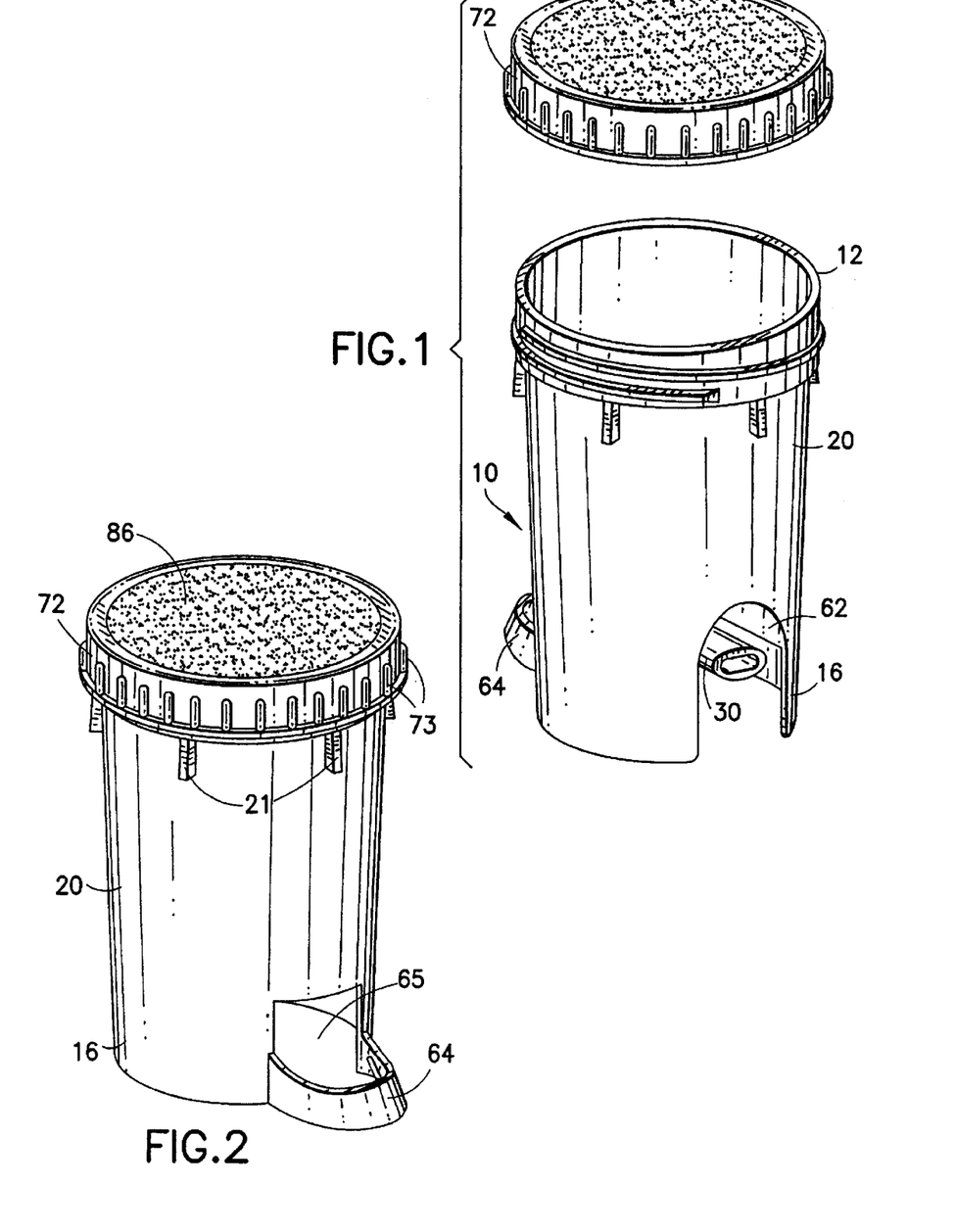
FIG. 1 is an exploded front perspective view of the biological fluid collection device with a pivotable faucet of the present invention.
FIG. 2 shows an assembled back perspective view of the biological fluid collection device in FIG. 1.
Figure 3:
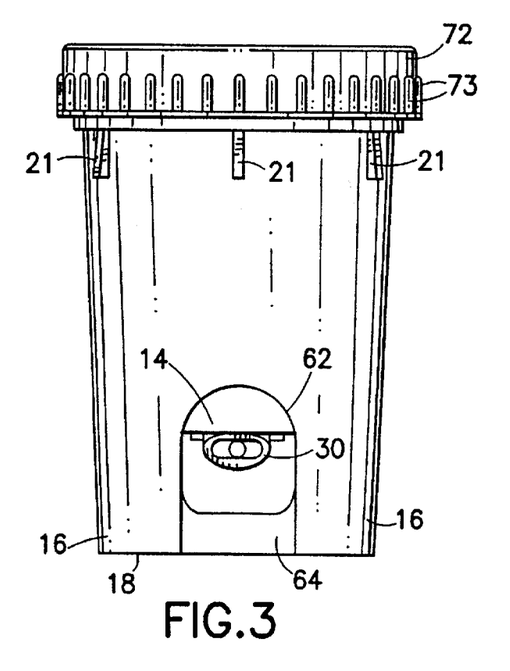
FIG. 3 shows a front view of the biological fluid collection device of FIG. 2.
Figure 4:
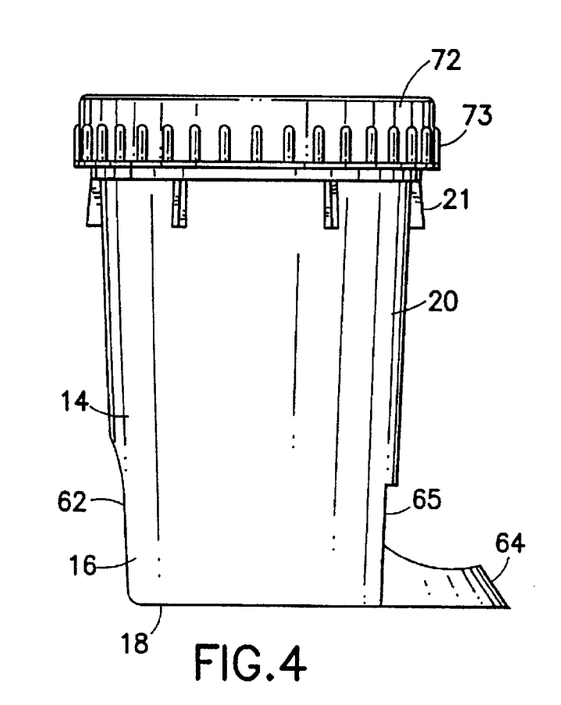
FIG. 4 illustrates a side view of the biological fluid collection device of FIG. 2.

A detent 64 is further included on annular skirt 16. Detent 64 is mounted on the back end of annular skirt 16 opposite recessed portion 62 for securing tube 40 in open position 34. Detent 64 has a planar bottom 19 for flat surface support with planar bottom 18 of annular skirt 16. Such structures are shown in FIG. 4. The function of detent 64 is to prevent further backward motion of tube 40 when pivoted into open position 34. Detent 64 also provides support to tube 40 when in open position 34.

Annular skirt 16 is further characterized by having an open area 65 adjacent to detent 64. Open area 65 is preferably rectangular in shape but is not limited to such a shape for device 8 to function. Other such shapes include semi-circles, triangles and elliptical shapes. A rectangular shape is preferred for open area 65 so that side walls 50 of tube 40 creates a frictional fit on the inner walls of open area 65. This frictional fit assists in the stability of tube 40 during transfer. Open area 65 also functions as a space for tube 40 to sit when in position 34.

Alternatively, orifice 22 and pivotable faucet 30 are disposed on a side wall 120 as shown in FIGS. 10 and 11. In this alternate embodiment, side wall 120 is further characterized by having a recessed portion 63 for securing tube 40 in a closed position 142 as shown in FIG. 10. This alternate embodiment is generally described as a container 110. Container 110 has a storage lid 94 disposed thereon.

Container 110 is characterized by an upper portion 112, a lower portion 114 and oblong side walls 120 therebetween. Storage lid 94 is disposed on upper portion 112. Preferably, storage lid 94 is a woven polyethylene material heat sealed on upper portion 112. However, storage lid 94 can be made of various thermoplastics. Such materials include polyethylene, styrene, polypropylene and polyester. Other attachment methods include snap fits, adhesive bonding and mechanical fasteners.

Lower portion 114 is characterized by having a substantially planar bottom 70 for providing flat surface support for container 110. Lower portion 114 further includes an array of snap fits 92 as shown in FIG. 10. The function of snap fits 92 is to hold tube 40 when container 110 is in storage prior to use. Preferably, snap fits 92 and container 110 are a unitary structure. However, snap fits 92 can be a separate component and be attached to lower portion 114 by several methods known to those skilled in the art. Such methods include heat welding, adhesive bonding, mechanical fasteners, ultrasonic welding, and snap fittings.

Side walls 120 is characterized by having a pair of depressions 90 as shown in FIG. 10 and FIG. 11. Depressions 90 allow the user to ergonomically and safely grasp container 110 without contaminating the fluid specimen inside.

In the preferred embodiment shown in FIGS. 1–9, container 10 has a lid 72 disposed on upper portion 12 for protecting the fluid in container 10 from contamination. In the alternate embodiment shown in FIGS. 10–11, storage lid 94 is disposed on upper portion 112 for protecting the contents inside container 110 prior to use. Such contents include tube 40 in snap fits 92. Unlike protective lid 72, storage lid 94 is not re-attached after collection. Protective lid 72 is placed on upper portion 12 after the specimen collection has been taken.

Protective lid 72 is further characterized by having at least one internal projection 82 for lockingly engaging at least one external projection 80 on side wall 20. External projection 80 is adjacent to upper portion 12. Preferably, internal projection 82 and external projection 80 are matching threads. However, it is within the purview of the invention for internal projection 82 and external projection 80 to be matching snap fits, or mechanical fasteners. In addition, internal projection 82 may be on side walls 20 and external projection 80 may be on lid 72.

When protective lid 72 is disposed on upper portion 12, a permanent and leak-resistant seal is formed. This seal prevents re-opening of lid 72 after collection of the biological fluid in container 10. The leak-resistant seal enables container 10 to provide safety from leaks or spills when the fluid is transferred into tube 40. After transfer, tube 40 is transported to the laboratory instead of container 10. Lid 72 provides protection from the biological fluid inside container 10 and protects the fluid specimen from contamination.

Protective lid 72 is further characterized by a plurality of ribs 73 circumferentially disposed on the edges of lid 72. Side walls 20 further includes a plurality of vertical ribs 21 also circumferentially disposed around the outside of container 10 adjacent to upper portion 12. The function of ribs 73 and vertical ribs 21 is to allow gripping of lid 72 and container 10 when attaching to form the permanent and leak resistant seal between lid 72 and container 10.

Cap 52 is further characterized by comprising a closure lid 74 hingedly attached to cap 52 for permanently sealing cap 52 after fluid collection. Closure lid 74 further includes a plug 75 off-centered from the center point of closure lid 74 to attach inside off-centered hole 54 of cap 52. A hinge 76 attaches closure lid 74 to cap 52. When plug 75 attaches to hole 54, a permanent and leak-resistant seal is formed. Tube 40 with transferred fluid from container 10 is transported to a laboratory for analysis with this safety feature which resists leaking or spilling fluid. There are many methods plug 75 can attach to hole 54. Such methods include matching snap fits, mechanical fasteners and latches known to those skilled in the art.

As shown in FIGS. 8 and 9, protective lid 72 it is further characterized by including a vent 84 for allowing air flow therethrough. Vent 84 includes an orifice 85. Fluid and air can penetrate orifice 85. A membrane 86 is disposed on the top of lid 72 to facilitate air flow from vent 84 during collection. Membrane 86 prevents fluid from escaping or penetrating while allowing air to permeate. Membrane 86 is disposed on lid 72 rather than in vent 84 to provide maximum air flow through orifice 85 and vent 84. Fluid is prevented from flowing through the rest of the lid 72 by membrane 86.

Operation of biological fluid collection device 8 begins with collecting a specimen in container 10. Collection can occur with or without collection tube 40 attached because pivotable faucet 30 has a closed position 32. Preferably, test tube 40 is attached to container 10 so that test tube 40 can be used as handle 60 during the collection process. After collection has taken place, protective lid 72 is disposed on upper portion 12 to prevent contamination and exposure to the specimen in container 10. Tube 40, if not attached, is attached to the container 10 by inserting hole 54 over male distal end 40 in releasably locking engagement. Male distal end 40 has a luer taper to match with hole 54 which has a corresponding taper. In closed position 32, closed bottom 42 of test tube 40 is perpendicular to container 10. Rotation of tube 40 towards recessed portion 62 allows pivotable faucet 30 to be in open position 34. In open position 34, closed bottom 42 of tube 40 is lower than lower portion 14 and fluid begins to flow through hole 54 and into tube 40. Once a sufficient amount of specimen has been transferred into tube 40, tube 40 is then rotated back into closed position 32. In closed position 32, no fluid is transferred from container 10. Tube 40 is then removed from pivotable faucet 30 and closure lid 72 is rotated on cap 52 such that plug 75 enters hole 54 for permanent and leak-resistant sealing. At this point, tube 40 is ready to be shipped to a laboratory for further analysis. Another tube may be attached to container 10 in a similar manner if more specimen samples are desired.

Test tube 40 can also be used with alternate collection container 110 as shown in FIGS. 10 and 11. Container 110 includes orifice 22 through side walls 120 at a low gravitational point inside container 110. Side walls 120 has recessed portion 63 for supporting tube 40 in closed position 142. Like the preferred embodiment, this alternate embodiment allows tube 40 to be used as a handle during the collection process. Container 110 is further characterized by having snap fits 92 mounted to lower portion 114 to hold tube 40 thereon during storage. Storage lid 94 is disposed over upper portion 112 and is removed before collection commences. Storage lid 94 is not replaced on upper portion 112 after the collection process has been completed. Side walls 120 further includes depressions 90 for assisting and gripping container 110.

Pivotable faucet 30, as shown in FIGS. 10 and 11, is rotated into closed position 142 and into recessed portion 63 when closed bottom 42 of tube 40 is above upper portion 112. Tube 40 again can be used as a handle for container 110 during collection. After collection, pivotable faucet 30 is rotated away from recessed portion 63 in an open position 144. Open position 144 is shown when closed bottom 42 of tube 40 is lowered for the fluid to flow through hole 54 and transfer into tube 40. Tube 40 can be rotated back into closed position 142 after the desire volume is transferred into tube 40. Tube 40 is removed and subsequently sealed by closure lid 74, similar to the preferred embodiment, for transport to a laboratory for analysis. At that point, another tube can be attached to container 110 if further specimen samples are desired. For both embodiments, it is preferred not to have faucet 30 in open position 34 or open position 144 during collection. Both embodiments preferably should have faucet 30 in closed position 32 or closed position 142 during collection in container 10 or container 110. This procedure is preferred because it reduces the risk of specimen leaks or spills during collection. During transfer into tube 40, faucet 30 is opened.

The embodiments depicted in FIGS. 1–11 are intended to merely be exemplary. They are not intended to depict all possible collection containers. Rather, pivotable faucet 30 and tube 40 can be used with any containers having the appropriate dimensions for mating male distal end 38 into hole 54. Pivotable faucet 30 can also be used in any desired angle of orientation. The present invention is able to control the volume of specimen transferred into tube 40 by pivotable faucet 30 without creating a potential for leakage or spills and without the use of blunt or sharp cannula. Thus, the present invention improves the safety and transfer control in biological fluid collection devices by eliminating the use of piercing members and controlling the transfer of the biological fluid by a pivotable faucet.

What is claimed is:

1. A biological fluid collection device, comprising:
   a container for holding the fluid having an upper open portion, a lower portion and side walls therebetween, said container further including an orifice therethrough at a low gravitational point inside said container;
   a projecting faucet pivotably attached to said container and in fluid communication with said orifice, said pivotable faucet having closed and open positions;
   a tube having a closed bottom, an open top and side walls therebetween, said tube further including a cap disposed on said open top, said cap having a hole therethrough for receiving said pivotable faucet in releasably locking engagement, said faucet rotated in said closed position when said tube is used as a handle for holding said container during collection, and said faucet rotated in said open position when fluid flows through said hole into said tube.

2. The biological fluid collection device of claim 1, wherein said orifice and said pivotable faucet are disposed on said lower portion.

3. The biological fluid collection device of claim 2, further comprising an annular skirt attached to said lower portion, said annular skirt having a planar bottom for flat surface support.

4. The biological fluid collection device of claim 3, wherein said annular skirt has a recessed portion for securing said tube in said closed position.

5. The biological fluid collection device of claim 3, further comprising a detent mounted on said annular skirt for securing said tube in said open position.

6. The biological fluid collection device of claim 5, wherein said detent has a planar bottom for flat surface support.

7. The biological fluid collection device of claim 1, further comprising a lid disposed on said upper open portion for protecting the fluid in said container from contamination.

8. The biological fluid collection device of claim 1, wherein said tube is non-evacuated.

9. The biological fluid collection device of claim 1, further comprising a closure lid hingedly attached to said cap for permanently sealing said cap after fluid collection.

10. A biological fluid collection device, comprising:
    a container having an upper portion, a lower portion, and side walls therebetween, said side walls having at least one external projection adjacent to said upper portion, said container further including an orifice through said lower portion at a low gravitational point on said lower portion;
    a projecting faucet pivotably attached to said lower portion and in fluid communication with said orifice, said pivotable faucet having closed and open positions;
    a protective lid having at least one internal projection for lockingly engaging said external projection of said side wall;
    a non-evacuated tube having a closed bottom, an open top and cylindrical side walls therebetween, said tube further including a cap disposed on said open top, said cap having a hole therethrough for receiving said pivotable faucet in releasably locking engagement, said pivotable faucet rotated in said closed position when said closed bottom of said tube is perpendicular to said container and said tube used as a handle for holding said container, and said pivotable faucet rotated in said open position when said closed bottom of said tube is lowered for the fluid to flow through said hole into said tube.

11. The biological fluid collection device of claim 10, further comprising an annular skirt attached to said lower portion, said annular skirt having a planar flat bottom for flat surface support.

12. The biological fluid collection device of claim 11, wherein said annular skirt has a recessed portion for securing said tube in said closed position.

13. The biological fluid collection device of claim 12, further comprising a detent mounted on said annular skirt for securing said tube in said open position.

14. The biological fluid collection device of claim 10, wherein said lid further comprises a vent for allowing air flow during fluid transfer from said container to said tube, said lid further including a membrane disposed thereon for allowing air flow through said vent and said membrane and preventing fluid flow through said membrane.

15. A biological fluid collection device, comprising:
    a container having an open portion, an upper portion, a lower portion and oblong side walls therebetween, said container further including an orifice and a recessed portion in said lower portion;
    a projecting faucet pivotably attached to said lower portion and in fluid communication with said orifice, said pivotable faucet having closed and open positions;
    a storage lid sealed on said open portion for protecting the contents of said container;
    a non-evacuated tube having a closed bottom, an open top and cylindrical side walls therebetween, said tube further including a cap disposed on said open top, said cap having a hole offset from the center of said cap for receiving said pivotable faucet in releasably locking engagement, said pivotable faucet rotated in said closed position and into said recessed portion when said closed bottom of said tube is above said upper portion and said tube used as a handle for said container, said pivotable faucet in said open position and rotated away from said recessed portion when said closed bottom of said tube is lowered for the fluid to flow through said hole into said tube.

16. The biological fluid collection device of claim 15, wherein said side walls of said container further include depressions for assisting in gripping said container.

17. The biological fluid collection device of claim 13, wherein said container further includes snap fits mounted to said lower portion to hold said tube thereon during storage.

* * * * *